United States Patent
Fan et al.

(10) Patent No.: US 9,138,577 B2
(45) Date of Patent: *Sep. 22, 2015

(54) ELECTRODE LEAD OF PACEMAKER AND PACEMAKER USING THE SAME

(75) Inventors: Li Fan, Beijing (CN); Liang Liu, Beijing (CN); Chen Feng, Beijing (CN); Li Qian, Beijing (CN); Yu-Quan Wang, Beijing (CN); Wen-Mei Zhao, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 386 days.

This patent is subject to a terminal disclaimer.

(21) Appl. No.: 13/527,820

(22) Filed: Jun. 20, 2012

(65) Prior Publication Data

US 2013/0110215 A1  May 2, 2013

(30) Foreign Application Priority Data

Oct. 28, 2011  (CN) .......................... 2011 1 0333509

(51) Int. Cl.
- A61N 1/00    (2006.01)
- A61N 1/05    (2006.01)
- A61N 1/362   (2006.01)
- H01B 7/04    (2006.01)

(52) U.S. Cl.
CPC ................ A61N 1/056 (2013.01); A61N 1/362 (2013.01); H01B 7/048 (2013.01)

(58) Field of Classification Search
CPC ............................... A61N 1/056; A61N 1/362
USPC ...................................... 607/5, 119; 600/373
See application file for complete search history.

(56) References Cited

U.S. PATENT DOCUMENTS

| | | | |
|---|---|---|---|
| 3,893,461 A * | 7/1975 | Preston | 607/17 |
| 5,713,945 A | 2/1998 | Fischer et al. | |
| 7,493,160 B2 | 2/2009 | Weber et al. | |
| 7,512,447 B2 * | 3/2009 | Marshall et al. | 607/122 |
| 7,596,415 B2 | 9/2009 | Brabec et al. | |
| 8,583,259 B2 * | 11/2013 | Liu et al. | 607/119 |
| 2004/0051432 A1 | 3/2004 | Jiang et al. | |
| 2006/0272701 A1 * | 12/2006 | Ajayan et al. | 136/263 |
| 2009/0062895 A1 | 3/2009 | Stahmann et al. | |

(Continued)

FOREIGN PATENT DOCUMENTS

| | | |
|---|---|---|
| CN | 1484275 | 3/2004 |
| CN | 1943805 | 4/2007 |

(Continued)

*Primary Examiner* — Niketa Patel
*Assistant Examiner* — William Levicky
(74) *Attorney, Agent, or Firm* — Novak Druce Connolly Bove + Quigg LLP (57) ABSTRACT

An electrode lead of a pacemaker includes at least one lead wire. The at least one lead wire includes at least one conductive core, a first insulating layer coated on an outer surface of the at least one conductive core, at least one carbon nanotube yarn spirally wound on an outer surface of the first insulating layer, and a second insulating layer coated on the surface of the at least one carbon nanotube yarn. One end of the at least one conductive core protrudes from the first insulating layer to form a naked portion. The at least one carbon nanotube yarn includes a number of carbon nanotubes joined end to end by van der Waals attractive forces. A pacemaker includes a pulse generator and the electrode lead electrically connected with the pulse generator.

13 Claims, 11 Drawing Sheets

(56) References Cited

U.S. PATENT DOCUMENTS

| | | |
|---|---|---|
| 2009/0194313 A1 | 8/2009 | Jiang et al. |
| 2009/0255706 A1 | 10/2009 | Jiang et al. |
| 2010/0147829 A1* | 6/2010 | Liu et al. ............ 219/546 |
| 2011/0026758 A1 | 2/2011 | Wang et al. |
| 2011/0160829 A1 | 6/2011 | Foster et al. |
| 2012/0053649 A1 | 3/2012 | Liu et al. |
| 2012/0271394 A1 | 10/2012 | Foster et al. |

FOREIGN PATENT DOCUMENTS

| | | |
|---|---|---|
| CN | 101499331 | 8/2009 |
| CN | 101757723 | 6/2010 |
| CN | 101925379 | 12/2010 |
| CN | 101927057 | 12/2010 |
| CN | 101990147 | 3/2011 |
| TW | 200945372 | 11/2009 |
| TW | 201039670 | 11/2010 |
| TW | I345792 | 7/2011 |

* cited by examiner

ELECTRODE LEAD OF PACEMAKER AND PACEMAKER USING THE SAME

This application claims all benefits accruing under 35 U.S.C. §119 from China Patent Application No. 201110333485.2, filed on Oct. 28, 2011, in the China Intellectual Property Office, the contents of which are hereby incorporated by reference. This application is related to common-assigned applications entitled, "METHOD FOR MAKING PACEMAKER ELECTRODE LEAD," filed on Jun. 20, 2012, and application Ser. No. 13/527,780; "ELECTRODE LEAD OF PACEMAKER AND PACEMAKER USING THE SAME," filed on Jun. 20, 2012, and application Ser. No. 13/527,782; "ELECTRODE LEAD OF PACEMAKER AND PACEMAKER USING THE SAME" filed on Jun. 20, 2012, 2011, and application Ser. No. 13/527,784; "PACEMAKERS AND PACEMAKER LEADS" filed on Jun. 20, 2012, and application Ser. No. 13/527,792; "PACEMAKERS AND PACEMAKER LEADS" filed on Jun. 20, 2012, and application Ser. No. 13/527,801; "ELECTRODE LEAD OF PACEMAKER AND PACEMAKER USING THE SAME" filed on Jun. 20, 2012, and application Ser. No. 13/527,808; "PACEMAKER ELECTRODE LEAD AND PACEMAKER USING THE SAME" filed on Jun. 20, 2012, and application Ser. No. 13/527,836; "PACEMAKER ELECTRODE LEAD AND PACEMAKER USING THE SAME" filed on Jun. 20, 2012, and application Ser. No. 13/527,849.

BACKGROUND

1. Technical Field

The present disclosure relates to an electrode lead of a pacemaker and a pacemaker using the same.

2. Description of Related Art

A pacemaker is an electronic therapeutic device that can be implanted in living beings. The pacemaker includes a battery, a pulse generator, and an electrode lead. The pulse generator is used to emit a pulsing current, via the electrode lead, to stimulate an organ such as a human heart, to work normally.

The electrode lead usually includes a lead wire made from metal or alloy. However, a mechanical strength and toughness of the lead wire decreases as the diameter decreases. The violence of a fierce seizure suffered by a patient or even the energetic long-term normal activities of the patient may cause damage to the implanted electrode lead, or the electrode lead may even be broken. Therefore, a working life of the electrode lead and of the pacemaker will be decreased, and safety of the patient may be threatened.

What is needed, therefore, is to provide an electrode lead of a pacemaker which has good mechanical strength, toughness, and small physical size, to improve the working life of the electrode lead and the pacemaker using thereof.

BRIEF DESCRIPTION OF THE DRAWING

Many aspects of the present disclosure can be better understood with reference to the following drawings. The components in the drawings are not necessarily to scale, the emphasis instead being placed upon clearly illustrating the principles of the present embodiments.

DETAILED DESCRIPTION

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean at least one.

Figure 1:
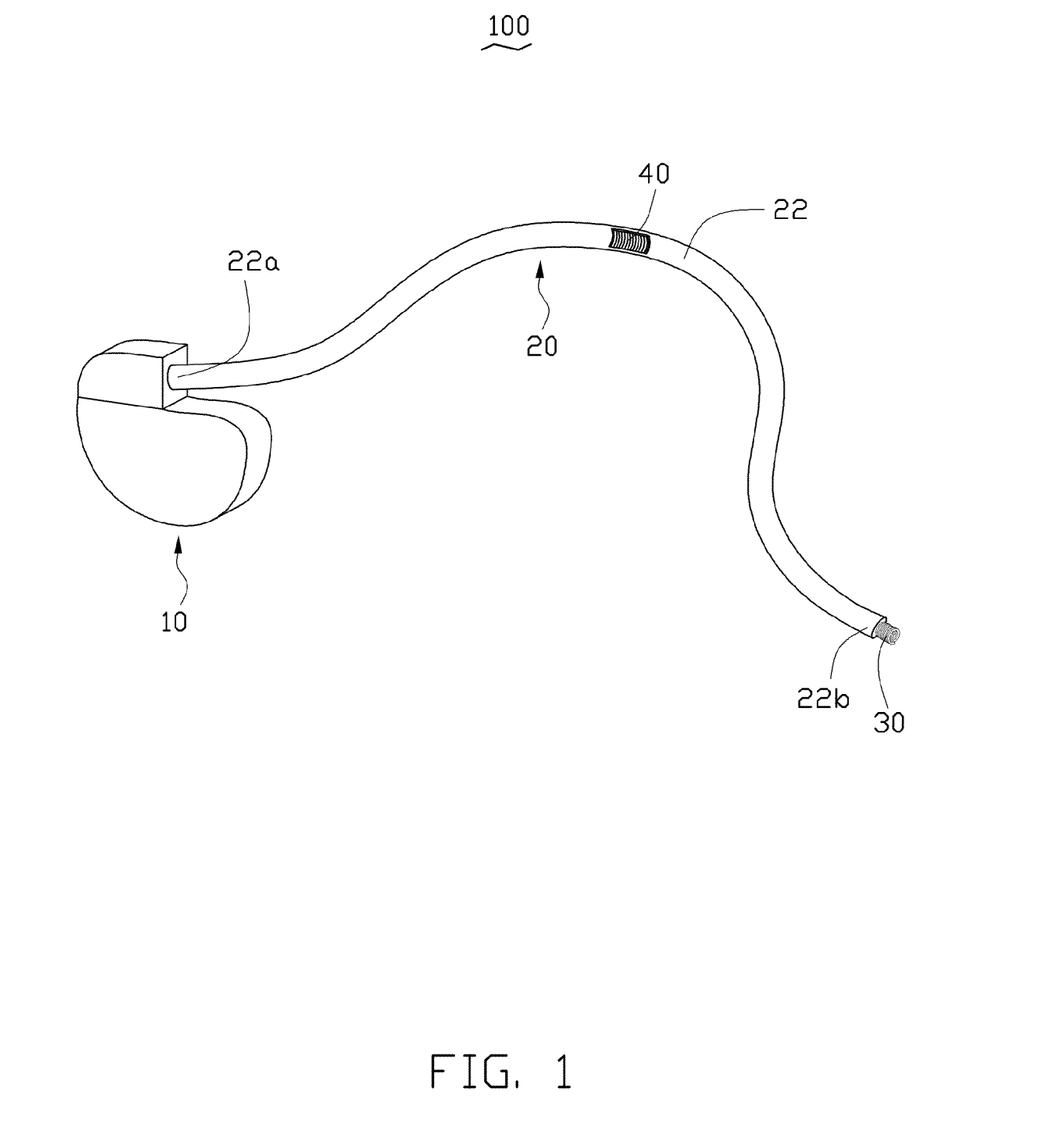
FIG. 1 is a view of one embodiment of a pacemaker.

Referring to FIG. 1, one embodiment of a pacemaker 100 includes a pulse generator 10 and an electrode lead 20 electrically connected with the pulse generator 10. The pulse generator 10 can be used to generate pulse signals to stimulate organs of living beings via the electrode lead 20.

The pulse generator 10 can include a shell (not labeled), a power source (not shown) and a control circuit (not shown). The power source and the control circuit are packaged in the shell. The power source can provide power for the control circuit. Batteries can be used as the power source, such as lithium ion batteries, fuel cells, and physical power batteries. In one embodiment, a lithium-iodine battery is the power source. The control circuit can include an output circuit and a sensing circuit. The output circuit can be used to generate the pulse signals. The sensing circuit can be used to receive electrical signals generated by the stimulated organs and feed these electrical signals back to the output circuit. The output circuit can adaptively adjust to output proper pulse signals according to the feedback of the sensing circuit. The organs can be a heart, brain, or stomach of living beings. In one embodiment, the organ is the heart of a human being. The pulse signals can be a square wave pulsing current. A pulse width of the pulse signals can be in a range from about 0.5 milliseconds to about 0.6 milliseconds. The pulse current can be generated by a charging-discharging process of a capacitor in the control circuit. The shell used for packaging can prevent interaction between the power source, the control circuit, and the living beings in which the pacemaker is implanted. A material of the shell can be a metal or alloy having inertness in the sense of biocompatibility, corrosion resistance, and toughness or rigidity of structure. In one embodiment, the material of the shell is titanium.

Referring FIG. 1, the electrode lead 20 can include at least one lead wire 22. The lead wire 22 has two ends opposite to each other along the extending direction of the lead wire 22. One end of the lead wire 22 is defined as a proximal end 22a, and the other end of the lead wire 22 is defined as a distal end 22b. The proximal end 22a is near and electrically connected with the pulse generator 10. The distal end 22b has a naked portion 30 which directly contacts the organs needing stimulation by the pulse signals.

Figure 2:
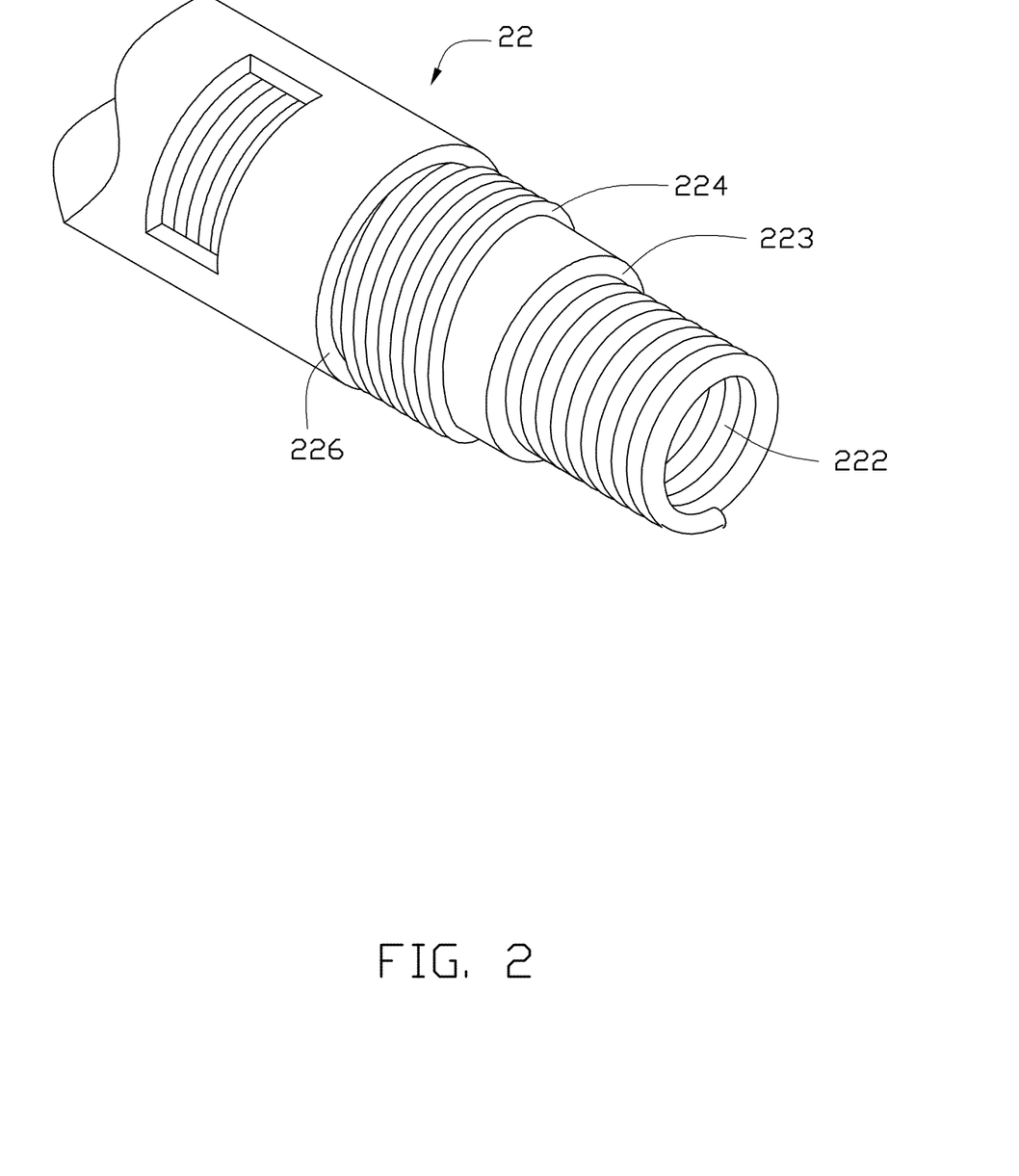
FIG. 2 is a ladder shaped sectional view of an embodiment of a lead wire of the pacemaker.

Referring to FIG. 1 and FIG. 2, the lead wire 22 can include at least one linear conductive core 222, a first insulating layer 223, at least one carbon nanotube yarn 224, and a second insulating layer 226. The first insulating layer 223 is coated on an outer surface of the at least one conductive core 222. The at least one carbon nanotube yarn 224 is spirally wound on an outer surface of the first insulating layer 223 to form a carbon nanotube layer. The second insulating layer 226 is coated on an outer surface of the carbon nanotube layer.

The conductive core 222 protrudes at the distal end 22b of the lead wire 22 to form the naked portion 30. The naked portion 30 is a part of the conductive core 222.

The conductive core 222 at the proximal end 22a is electrically connected with a negative electrode of the power source via the control circuit. The conductive core 222 at the distal end 22b directly contacts the organs through the naked portion 30.

The conductive core 222 can be a hollow or a cylindrical structure of solid material. A material of the conductive core 222 can be a metal or a composite formed of metal and other conductive materials. The metal can be MP35N, 35NLT, stainless steel, carbon fiber, tantalum, titanium, zirconium, niobium, titanium alloy, copper, silver, platinum, platinum-yttrium alloy, or platinum-palladium alloy. MP35N is an alloy including 35Co-35Ni-20Cr-10Mo, and titanium is about 1% by weight in the alloy. 35NLT is also an alloy including 35Co-35Ni-20Cr-10Mo, and the percentage of titanium is about 0.01% by weight in the alloy. The composite can be a composite material of metal and carbon fiber. In one embodiment, the material of the conductive core 222 is platinum.

The first insulating layer 223 and second insulating layer 226 can be fabricated by a flexible material having biocompatibility, such as silicon, polyurethane, polytetrafluoroethylene, or a copolymer of silicon and polyurethane. In one embodiment, the material of the first insulating layer 223 and the second insulating layer 226 is silicon. A thickness of the first insulating layer 223 or the second insulating layer 226 can be in a range from about 1 micron to about 50 microns.

The at least one carbon nanotube yarn 224 can be a non-twisted carbon nanotube yarn, a twisted carbon nanotube yarn, or any combination thereof.

Figure 3:
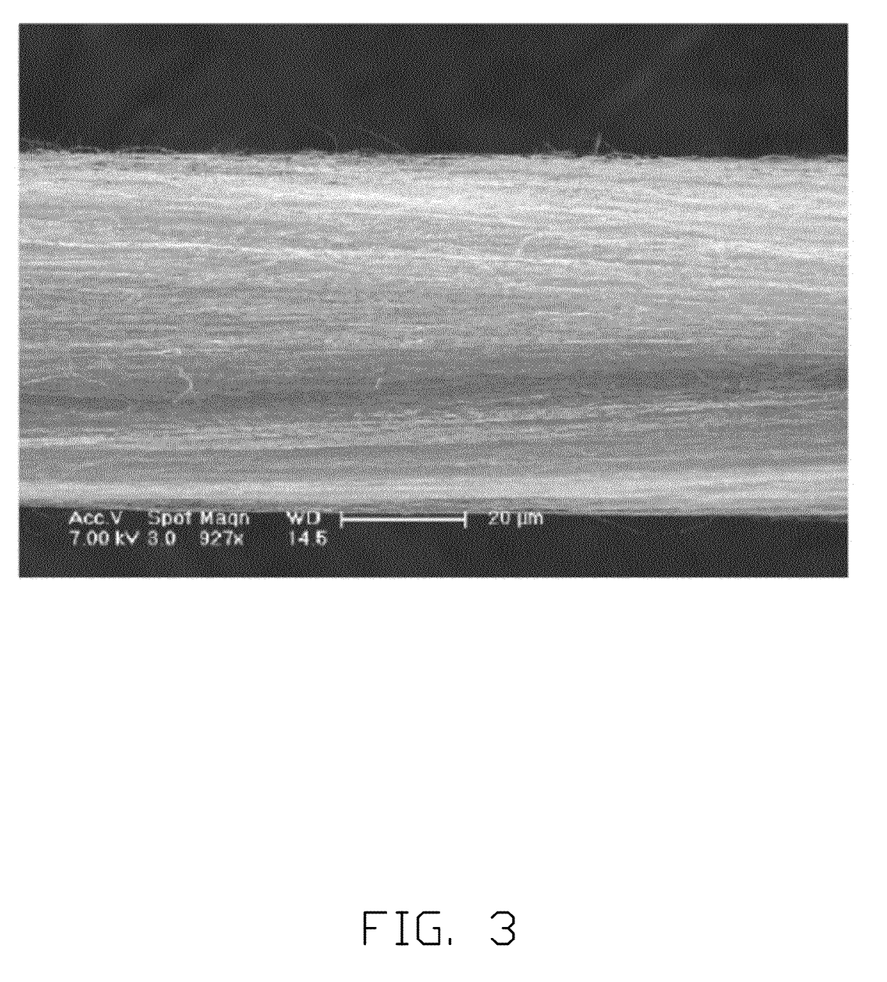
FIG. 3 shows a scanning electron microscope (SEM) image of a non-twisted carbon nanotube yarn.

Referring to FIG. 3, the non-twisted carbon nanotube yarn is a free-standing structure consisting of a plurality of carbon nanotubes. A majority of the plurality of carbon nanotubes extend in substantially the same direction and parallel to each other. In addition, the majority of the carbon nanotubes are joined end to end by van der Waals attractive forces. Each carbon nanotube in the majority of the carbon nanotubes is joined with the adjacent carbon nanotube lengthwise by van der Waals attractive forces. A minority of the plurality of carbon nanotubes is randomly arranged in the non-twisted carbon nanotube yarn, and has a very small or negligible effect on the majority of the carbon nanotubes in view of the arrangement thereof. The non-twisted carbon nanotube yarn includes a plurality of successive and preferred-oriented carbon nanotube segments. The plurality of carbon nanotube segments are joined end to end by van der Waals attractive forces. Each of the carbon nanotube segments includes a plurality of carbon nanotubes substantially parallel with each other. The carbon nanotubes in parallel are joined side by side by van der Waals attractive forces. The free-standing structure of the non-twisted carbon nanotube yarn is a result of van der Waals attractive forces acting on the carbon nanotubes joined end to end and side by side. A diameter of the non-twisted carbon nanotube yarn can be in a range from about 0.5 nanometers to about 100 microns.

The non-twisted carbon nanotube yarn can be formed by the steps of: S(a), choosing a carbon nanotube segment having a predetermined width from a carbon nanotube array by a drawing tool; and S(b), moving the drawing tool to pull the chosen carbon nanotube segment at a predetermined speed, thereby pulling out a continuous carbon nanotube yarn including the plurality of carbon nanotube segments joined end-to-end by van der Waals attractive forces therebetween. Examples of the non-twisted carbon nanotube wire are taught by US Patent Application Publication US 2007/0166223 to Jiang et al.

Figure 4:
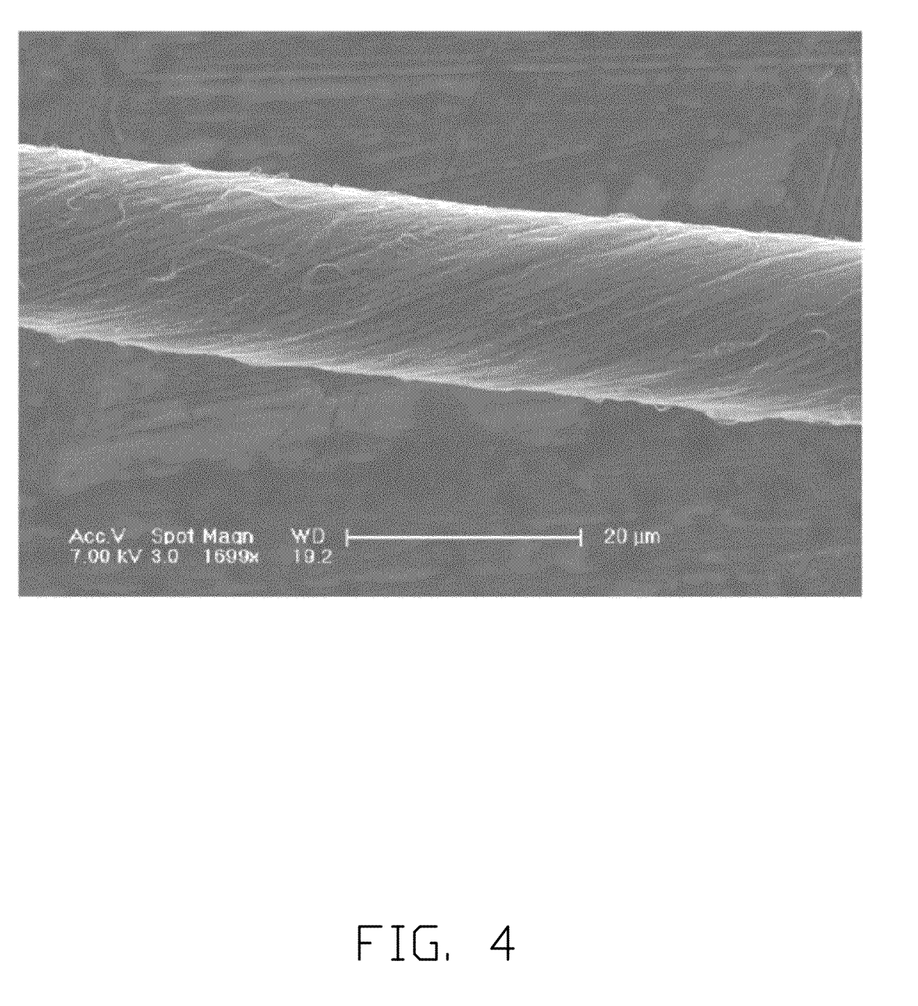
FIG. 4 shows a SEM image of a twisted carbon nanotube yarn.

Referring to FIG. 4, the twisted carbon nanotube yarn can be formed by twisting the non-twisted carbon nanotube yarn by using a mechanical force to turn the two ends of the non-twisted carbon nanotube yarn in opposite directions. The twisted carbon nanotube yarn includes a plurality of carbon nanotubes oriented around the central axis of the twisted carbon nanotube yarn. The carbon nanotubes are aligned helically around the central axis of the twisted carbon nanotube yarn.

The non-twisted carbon nanotube yarn and the twisted carbon nanotube yarn can be treated with a volatile organic solvent. After being soaked by the organic solvent, the carbon nanotubes which are adjacent and substantially parallel to each other in the non-twisted or twisted carbon nanotube yarn will bundle together, due to the surface tension of the organic solvent when the organic solvent volatilizes. A specific surface area and a viscosity of the carbon nanotube yarn will decrease, and a density and strength of the carbon nanotube yarn will increase. A tensile strength of the twisted carbon nanotube yarn can be greater than 1200 Mega Pascals (MPa). The tensile strength can reach about 1.5 Giga Pascals (GPa), if the diameter of the twisted carbon nanotube yarn decreases to about 10 microns. The volatile organic solvent can be ethanol, methanol, acetone, dichloroethane, chloroform, or any combination thereof. In one embodiment, the volatile organic solvent is ethanol. The carbon nanotube yarn 224 can be a pure carbon nanotube structure. The pure carbon nanotube structure consists of pristine carbon nanotubes. The characterization "pristine" signifies that the carbon nanotubes are unfunctionalized or not chemically modified.

The at least one carbon nanotube yarn 224 can include a plurality of carbon nanotube yarns 224. The plurality of carbon nanotube yarns 224 can be arranged as a bundle or a twisted cable by twisting the bundle to increase the strength thereof.

The at least one carbon nanotube yarn 224 is electrically connected with a positive electrode of the power source via the sensing circuit.

The at least one carbon nanotube yarn 224 can be spirally wound on the outer surface of the first insulating layer 223 to completely cover the outer surface. The at least one carbon nanotube yarn 224 can also be spirally wound on a part of the outer surface of the first insulating layer 223 to partly cover the outer surface. Because the carbon nanotube yarn 224 is sticky, the carbon nanotube yarn 224 can directly adhere on the outer surface of the first insulating layer 223 without a binder after spiral winding. A screw pitch of the spirally wound carbon nanotube yarn 224 can be in a range from about 0 microns to about 5 microns. The pitch can be gradually increased from the proximal end 22a to the distal end 22b. If a patient, with an implanted pacemaker 100 suffers a physical abnormal pain such as a fierce seizure, a typical conductive core is fragile and may easily damage or break. However, the carbon nanotube yarn 224 is harder to break due to a good flexibility. In addition, the gradually increasing screw pitch of the carbon nanotube yarn 224 can provide a varied elasticity and thus greater deformability of the lead wire 22 when stretched or bent. Therefore, the chance of an injury to the organs of the patient due to an excessively brittle lead wire 22 can be decreased.

Figure 5:
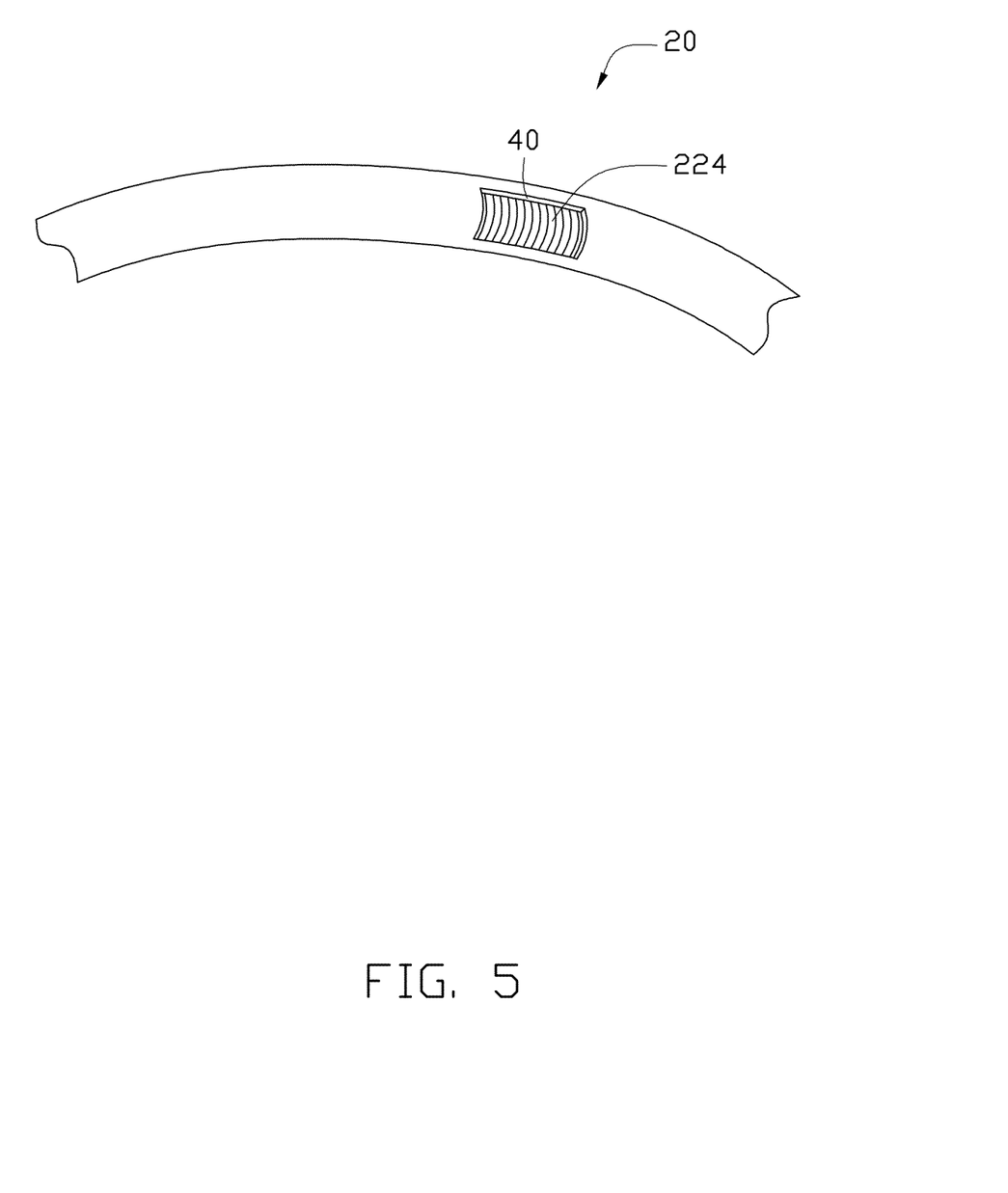
FIG. 5 shows a detailed view of an exposed portion of an embodiment of the pace maker.

Referring to FIG. 1 and FIG. 5, the lead wire 22 can include an exposed portion 40 along the extending direction thereof, and parts of the carbon nanotube yarn 224 are exposed from the exposed portion 40. More specifically, the second insulating layer 226 can define at least one opening to form the exposed portion 40. The parts of the carbon nanotube yarn 224 can be exposed from the opening. The at least one opening can be a C-shaped structure around an axis of the lead wire 22 to prevent the second insulating layer 226 from falling off the opening. The at least one opening can also include one or more spaced through holes formed on the second insulating layer 226. The portion of the carbon nanotube yarn 224 exposed from the exposed portion 40 can directly contact a tissue fluid of the living beings in which the pacemaker 100 is implanted. The exposed portion 40 of the carbon nanotube yarn 224 can act as a sensing electrode of the pacemaker 100 to sense signals of the organs such as beating. The sensed signals can be fed back to the output circuit to adjust the pulse signals to an appropriate value for regulating the organ to work normally. The carbon nanotube yarn 224 has a large surface area which can increase the sensitivity and sensing efficiency of the carbon nanotube yarn in the exposed portion 40 as the sensing electrode. The exposed portion 40 can be spaced from the naked portion 30. The exposed portion 40 can be disposed near the proximal end 22a or the naked portion 30. A distance between the exposed portion 40 and the naked portion 30 along the extending direction of the lead wire 22 can be in a range from about 2 centimeters to about 10 centimeters. The lead wire 22 can include a plurality of exposed portions 40 along the extending direction thereof. The plurality of exposed portions 40 can be spaced apart from each other.

Figure 6:
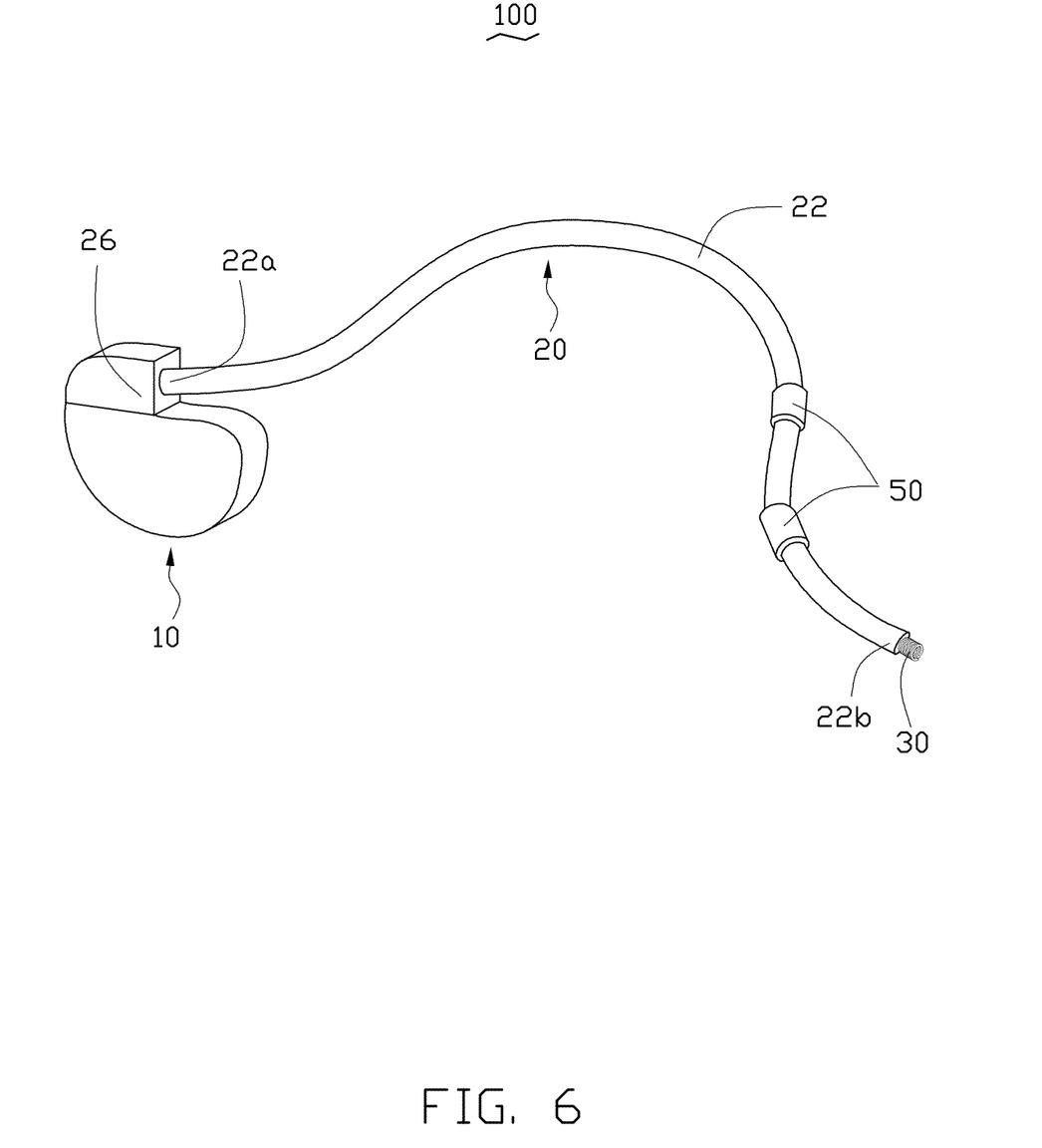
FIG. 6 shows a view of an embodiment of the pacemaker including a ring electrode.

Referring to FIG. 6, in one embodiment, there can have no exposed portion 40 in the lead wire 22. Instead, the pacemaker 100 can include one or more ring shaped electrodes 50 disposed on an outer surface of the lead wire 22. Each of the one or more ring-shaped electrodes 50 is electrically connected with carbon nanotube yarn 224 of the lead wire 22. The one or more ring-shaped electrodes 50 are used as the sensing electrode of the pacemaker 100. A material of the one or more ring-shaped electrodes 50 can be a conductive biocompatible material, such as metal or a carbon containing material. The carbon containing material can be carbon fibers or carbon nanotubes. In one embodiment, the one or more ring-shaped electrodes 50 are made of titanium.

Figure 7:
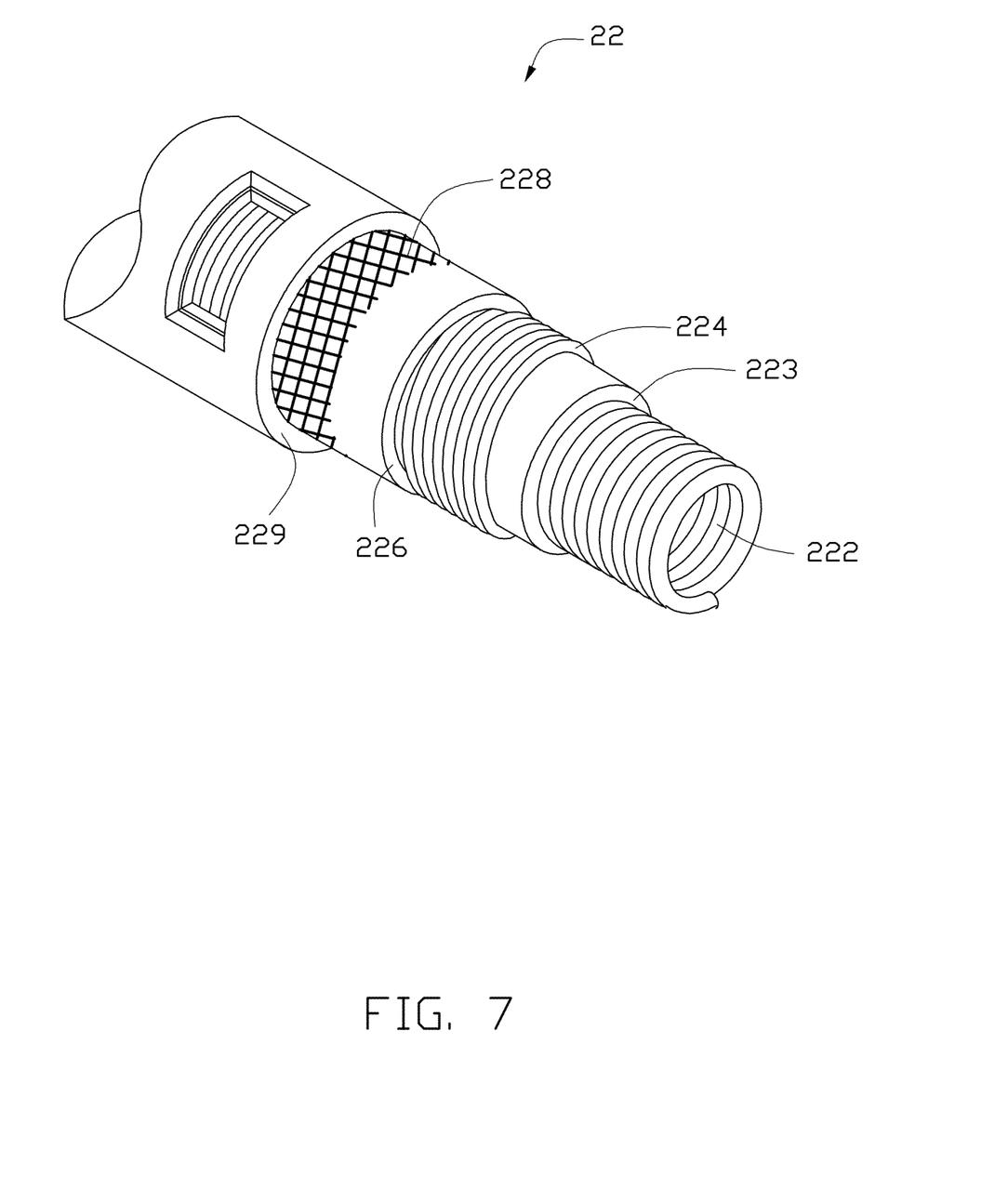
FIG. 7 shows a sectional view of an embodiment of the lead wire with a shielding layer disposed on an outer surface of a second insulating layer and with some layers peeled away.

Referring to FIG. 7, the lead wire 22 can include a shielding layer 228 and a third insulating layer 229. The shielding layer 228 is disposed on an outer surface of the second insulating layer 226. The third insulating layer 229 is coated on an outer surface of the shielding layer 228. The shielding layer 228 can be a successive film or a network structure made of a conductive material. A material of the shielding layer 228 can be metal, a carbon containing material, or combinations thereof. The carbon containing material can be carbon fiber, graphene, carbon nanotube, or combinations thereof. A material of the third insulating layer 229 can be the same as the material of the first insulating layer 223 and the third insulating layer 229. In one embodiment, the material of the third insulating layer 229 is polytetrafluoethylene. A biological coating can be coated on an outer surface of the third insulating layer 229. The biological coating can increase the biological compatibility of the electrode lead 20 and can be used as a bactericide or a disinfectant. A material of the biological coating can be zirconia or zirconium nitride. The lead wire 22 having the shielding layer 228 and the third insulating layer 229 can also include the openings to expose parts of the carbon nanotube yarn for directly contacting the tissue fluid of the living beings.

Figure 8:
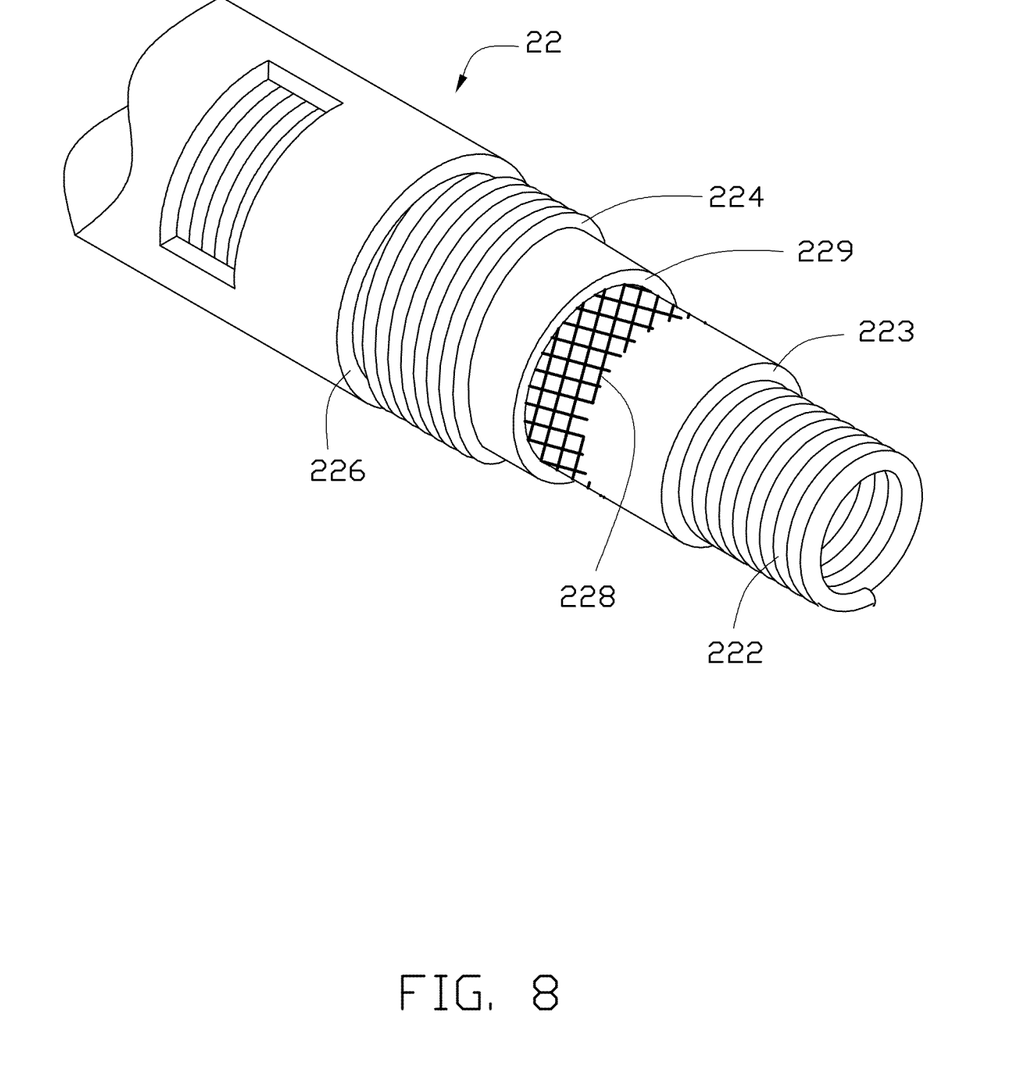
FIG. 8 shows a sectional view of an embodiment of the lead wire with the shielding layer disposed on an outer surface of a first insulating layer and with some layers peeled away.

Referring to FIG. 8, the shielding layer 228 and the third insulating layer 229 can be disposed between the first insulating layer 223 and the carbon nanotube layer formed by the yarn 224. Specifically, the structure of the lead wire 22 from the center out includes the conductive core 222, the first insulating layer 223, the shielding layer 228, the third insulating layer 229, the spirally wound carbon nanotube yarn 224, and the second insulating layer 226. The opening runs through the second insulating layer 226 to the third insulating layer 229 to expose parts of the carbon nanotube yarn 224.

The electrode lead 20 can include a plurality of lead wires 22 to stimulate different organs of the living being.

Figure 9:
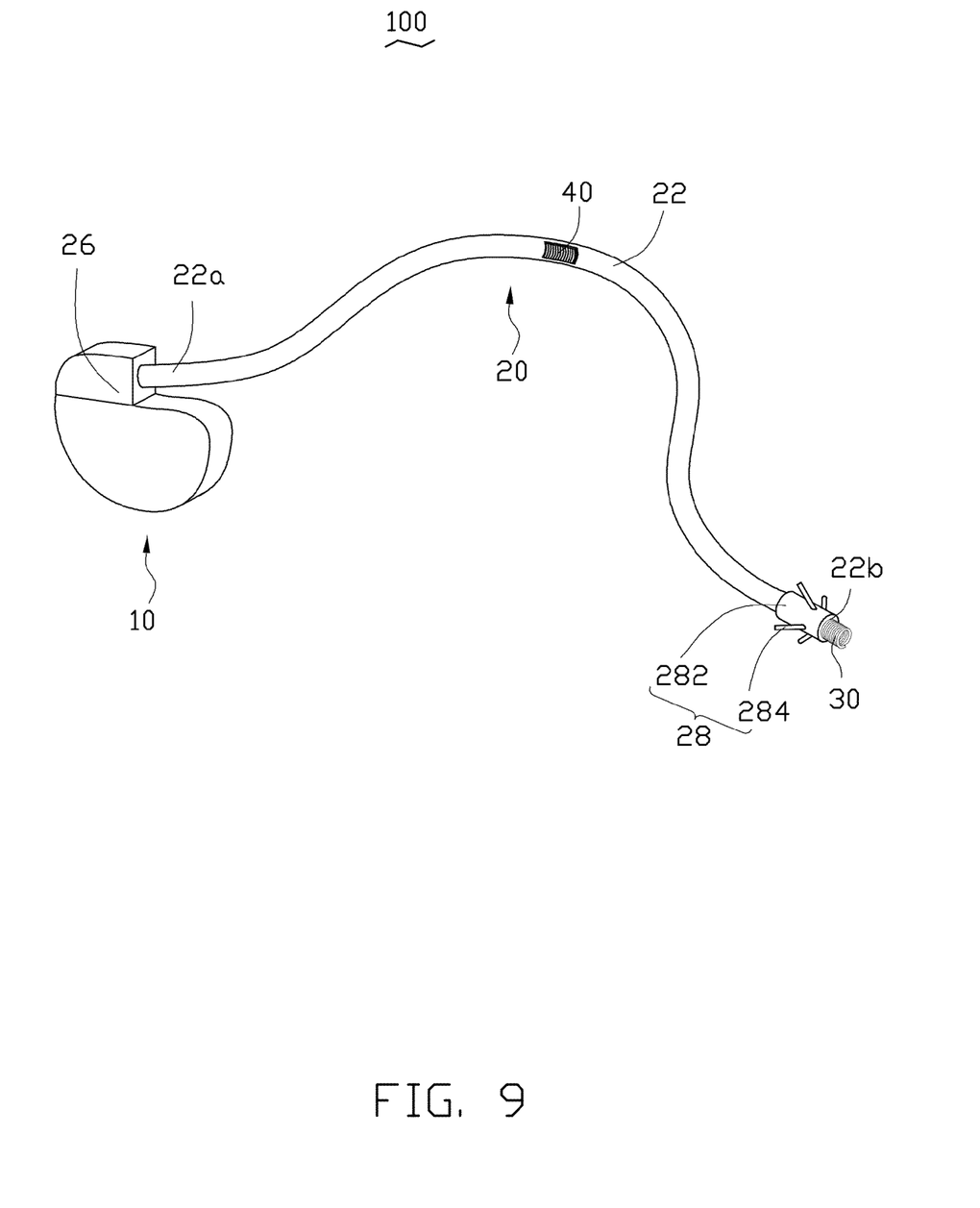
FIG. 9 is a view of an embodiment of the pacemaker with a connector and a fixture.

Referring to FIG. 9, the pacemaker 100 can further include a connector 26 and a fixture 28. The proximal end 22a of the lead wire 22 can be electrically connected with and fixed to the pulse generator 10 via the connector 26. The connector 26 can include a conductive contact member (not shown). The conductive contact member includes two opposite ends. One end of the conductive contact member is electrically connected and in contact with the control circuit in the pulse generator 10. The other end is electrically connected and in contact with the proximal end 22a of the lead wire 22. Thereby the lead wire 22 can be electrically connected with the control circuit in the pulse generator 10 to transmit the pulse signals. A material of the connector 26 can be the same as the material of the shell. In one embodiment, the material of the connector 26 is titanium. A material of the fixture 28 can be a polymer such as polyurethane or silicon rubber. The fixture 28 can include a fixing ring 282 and a plurality of fixing wings 284. The fixing ring 282 can be a cylindrical structure. The plurality of fixing wings 284 can be rod shaped. The plurality of fixing wings 284 forms a branch axis diverging from a center line or axis of the fixing ring 282, to form a barb structure. A diverging direction deviates from the extending direction of the distal end 22b. An angle between the extending direction of each fixing wing 284 and the center line of the fixing ring 282 can be in a range from about 30 degrees to about 60 degrees. The distal end 22b is fixed to the organ by the fixing ring 282 to prevent the electrode lead 20 from moving or falling off the organ. The fixture 28 can also be a protrusion or helical structure as long as the electrode lead 20 can be tightly fixed in the organ of living beings by fibrous tissues of the organ of living beings wrapping the fixture 28.

The connector 26 and the fixture 28 are not necessary elements in the pacemaker 100. The proximal end 22a of the lead wire 22 can be directly connected with the control circuit. In addition, the distal end 22b of the lead wire 22 can be wrapped by the fibrous tissues of the organ of living beings to fix the electrode lead 20 in the target organs after a period of time after the electrode lead 20 has been implanted.

A working process of the pacemaker 100 acting on the heart of a human being can be described below. The positive electrode of the power source is electrically connected with the carbon nanotube yarn 224, and the negative electrode of the power source is electrically connected with the proximal end 22a of the lead wire 22 via the control circuit. The pulse signals are generated by the pulse generator 10 and transmitted to the naked portion 30 of the distal end 22b which directly stimulates the heart. A heartbeat frequency or a series of heartbeat frequencies can be sensed by detecting potential differences between the naked portion 30 and the carbon nanotube yarn 224. The potential differences are fed back to the control circuit to adjust the pulse signals to make the heart beat normally. If the ring-shaped electrode 50 is used instead of the exposed portion 40, the sensing signals can be obtained by detecting the potential differences between the ring shaped electrode 50 and the naked portion 30. In addition, a plurality of electrode lead 20 can be used to stimulate different organs in the human being.

Figure 10:
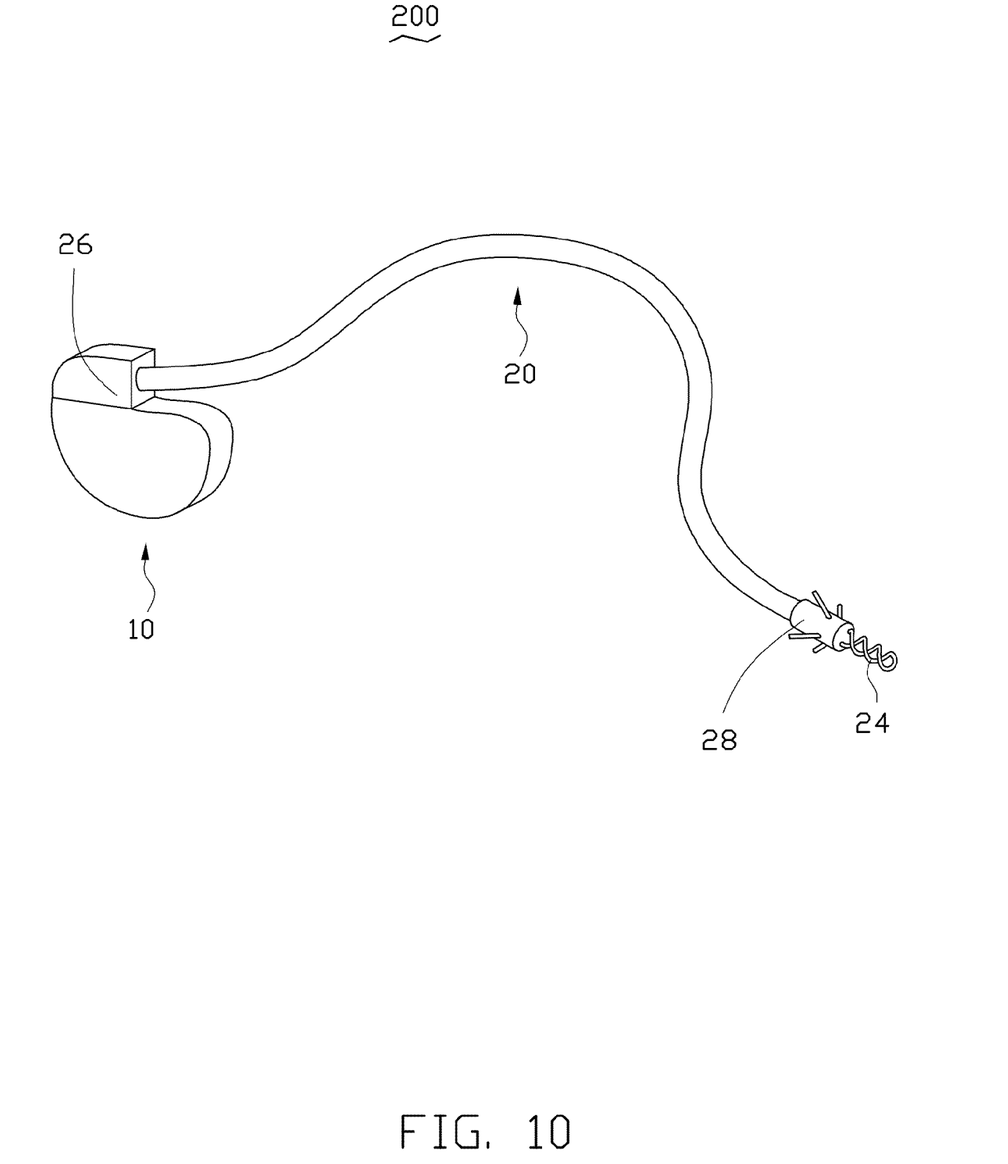
FIG. 10 is a view of another embodiment of a pacemaker.
Figure 11:
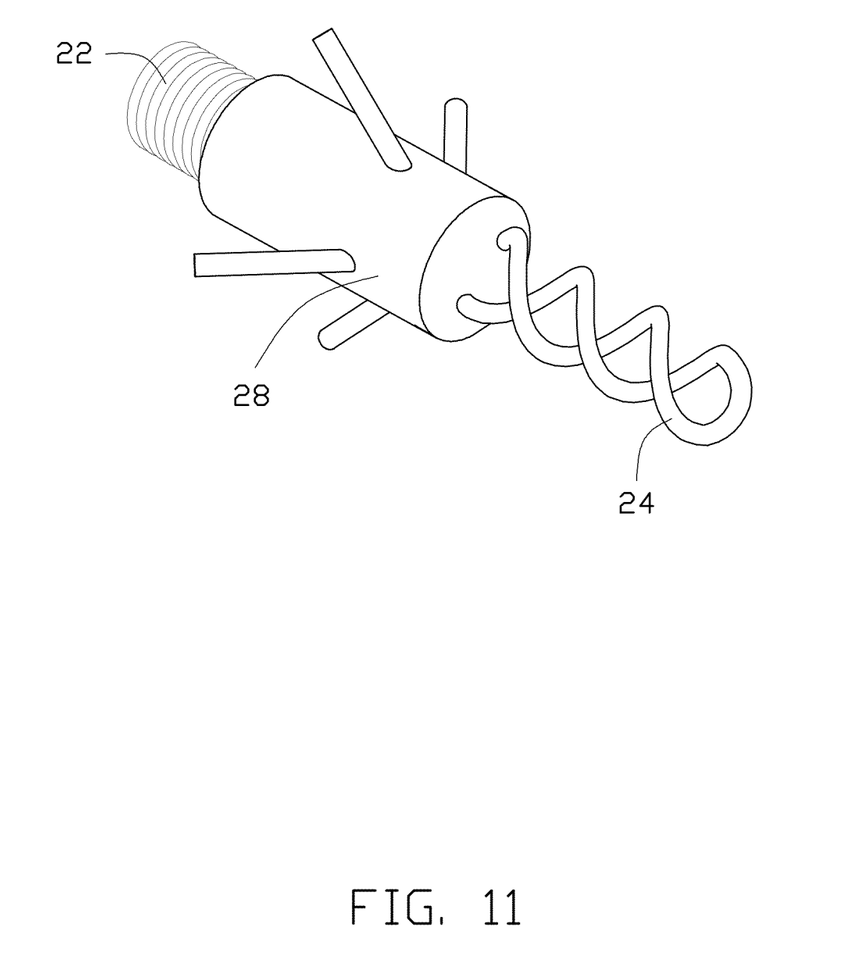
FIG. 11 is a view of an embodiment of an electrode tip of the pacemaker.

Referring to FIG. 10 and FIG. 11, another embodiment of a pacemaker 200 is provided. The structure of the pacemaker 200 is similar to the structure of the pacemaker 100. The difference between the two pacemakers is that the electrode lead 20 further includes an electrode tip 24 with two opposite ends. One end of the electrode tip 24 is electrically connected with the distal end 22b of the lead wire 22. The other end acts as a contact end directly contacting and stimulating the heart. The fixture 28 can protect and maintain the integrity of a joint between the electrode tip 24 and the distal end 22b of the lead wire 22. The lead wire 22 will function only as a pulse signal transmitter if the electrode tip 24 is used in the pacemaker. Under this situation, there will be no need for a naked distal end 22b of the lead wire 22. The electrode tip 24 can be welded as an integrated structure. The electrode tip 24 can be cylindrical, helical, or ring shaped. In one embodiment, the electrode tip 24 is helical. A length of the electrode tip 24 can be in a range from about 0.5 microns to about 2 microns. A material of the electrode tip 24 can be the same as the material of the conductive core 222. A porous material to ensure biocompatibility can be coated on an outer surface of the electrode tip 24. The porous material can increase the sensing area of the electrode tip 24, thereby increasing the sensitivity and sensing efficiency of the pacemaker 200.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. An electrode lead of a pacemaker comprising at least one lead wire, wherein the at least one lead wire comprises:
   at least one conductive core;
   a first insulating layer coated on an outer surface of the at least one conductive core;
   at least one carbon nanotube yarn spirally wound on an outer surface of the first insulating layer to form a carbon nanotube layer, wherein the at least one carbon nanotube yarn is combined with the first insulating layer by van der Waals attractive forces; and
   a second insulating layer coated on a surface of the carbon nanotube layer;
   wherein one end of the at least one conductive core protrudes from the first insulating layer to form a naked portion, and the at least one carbon nanotube yarn comprises a plurality of carbon nanotubes joined end to end by van der Waals attractive forces.

2. The electrode lead of claim 1, wherein the lead wire further comprises at least one exposed portion along an extending direction of the lead wire, the at least one exposed portion is spaced from the naked portion, and at least a part of the carbon nanotube layer is exposed through the at least one exposed portion.

3. The electrode lead of claim 2, wherein a distance between the at least one exposed portion and the naked portion is in a range from about 2 centimeters to about 10 centimeters.

4. The electrode lead of claim 2, wherein the at least one exposed portion is a plurality of exposed portions spaced from each other along the extending direction of the lead wire.

5. The electrode lead of claim 2, wherein the lead wire further comprises a third insulating layer and a shielding layer disposed between the carbon nanotube layer and the first insulating layer, the shielding layer is disposed on the outer surface of the first insulating layer, and the third insulating layer is coated on an outer surface of the shielding layer.

6. The electrode lead of claim 2, wherein the lead wire further comprises a shielding layer disposed on an outer surface of the second insulating layer and a third insulating layer disposed on an outer surface of the shielding layer.

7. The electrode lead of claim 1, wherein the naked portion is a protrusion and the protrusion is helical.

8. The electrode lead of claim 1, wherein a screw pitch of the spirally wound carbon nanotube yarn is in a range from about 0 microns to about 5 microns.

9. A pacemaker comprising:
   a pulse generator, the pulse generator comprising:
      a power source comprising a positive electrode and a negative electrode; and
      a control circuit; and
   an electrode lead electrically connected with the pulse generator, the electrode lead comprising at least one lead wire, wherein the at least one lead wire comprises:
      at least one conductive core;
      a first insulating layer coated on an outer surface of the at least one conductive core;
      at least one carbon nanotube yarn spirally wound on an outer surface of the first insulating layer to form a carbon nanotube layer; and
      a second insulating layer coated on a surface of the carbon nanotube layer;
      wherein one end of the at least one conductive core protrudes from the first insulating layer to form a naked portion, and the at least one carbon nanotube yarn comprises a plurality of carbon nanotubes joined end to end by van der Waals attractive forces; and
   wherein the power source, the control circuit, and the lead wire are electrically connected in series, the lead wire comprises a proximal end and a distal end opposite to the proximal end, the naked portion is located in the distal end and adapted to be located to directly contact and stimulate an organ, the conductive core at the proximal end is electrically connected with the negative electrode via the control circuit, and the at least carbon nanotube yarn at the proximal end is electrically connected with the positive electrode via the control circuit.

10. The pacemaker of claim 9 further comprising:
    a connector to connect the pulse generator to the electrode lead; and
    a fixture adapted to be located to fix the electrode lead to an organ.

11. The pacemaker of the claim 10, wherein the fixture comprises a fixing ring and a plurality of fixing wings disposed on an outer surface of the fixing ring.

12. The pacemaker of the claim 9, wherein the electrode lead further comprises an electrode tip electrically connected with the distal end of the lead wire.

13. An electrode lead of a pacemaker comprising at least one lead wire, wherein the at least one lead wire comprises:
    at least one conductive core;

a first insulating layer coated on an outer surface of the at least one conductive core;

at least one carbon nanotube yarn spirally wound on an outer surface of the first insulating layer to form a carbon nanotube layer, wherein a screw pitch of the at least one carbon nanotube yarn gradually increases along an extending direction of the at least one carbon nanotube yarn; and a second insulating layer coated on a surface of the carbon nanotube layer;

wherein one end of the at least one conductive core protrudes from the first insulating layer to form a naked portion, and the at least one carbon nanotube yarn comprises a plurality of carbon nanotubes joined end to end by van der Waals attractive forces.

* * * * *